US00PP28822P2

(12) United States Plant Patent
Smit

(10) Patent No.: US PP28,822 P2
(45) Date of Patent: Dec. 26, 2017

(54) ***PEPEROMIA* PLANT NAMED 'RED LOG'**

(50) Latin Name: ***Peperomia* hybrid**
Varietal Denomination: Red Log

(71) Applicant: Obed Jacob Smit, Sappemeer (NL)

(72) Inventor: Obed Jacob Smit, Sappemeer (NL)

(73) Assignee: Eden CollecTion B.V., Sappemeer (NL)

( * ) Notice: Subject to any disclaimer, the term of this patent is extended or adjusted under 35 U.S.C. 154(b) by 0 days.

(21) Appl. No.: 15/330,475

(22) Filed: Sep. 26, 2016

(51) Int. Cl.
*A01H 5/02* (2006.01)

(52) U.S. Cl.
USPC ..... Plt./373

(58) Field of Classification Search
USPC ..... Plt./373
See application file for complete search history.

*Primary Examiner* — Annette H Para

(57) ABSTRACT

A new cultivar of *Peperomia* plant named 'Red Log' that is characterized by leaves that are dark green on the upper surface and red on the lower surface, an upright habit and strong stems.

1 Drawing Sheet

Botanical classification: *Peperomia* hybrid.
Variety denomination: 'Red Log'.

BACKGROUND OF THE INVENTION

The present invention relates to a new and distinct cultivar of *Peperomia* plant botanically known as *Peperomia* hybrid and hereinafter referred to by the cultivar name 'Red Log'.

'Red Log' originated from the crossing of the female or seed parent, an unnamed *Peperomia verticillata* cultivar and the male or pollen parent, an unnamed *Peperomia rubella* cultivar. The crossing was conducted in 2013 in Sappemeer, Netherlands. The resulting seeds were subsequently planted and grown. The cultivar 'Red Log' was selected by the inventor in 2014 in a controlled environment as a single plant within the progeny of the stated cross in a cultivated area of Sappemeer, Netherlands.

Asexual reproduction of the new cultivar 'Red Log' first occurred by leaf cuttings in 2014 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'Red Log'. These traits in combination distinguish 'Red Log' as a new and distinct cultivar apart from other existing varieties of *Peperomia* known by the inventor.

1. *Peperomia* 'Red Log' exhibits leaves that are dark green on the upper surface and red on the lower surface.
2. *Peperomia* 'Red Log' exhibits an upright habit.
3. *Peperomia* 'Red Log' exhibits strong stems.

The closest comparison cultivars are *Peperomia* 'Belly Button' (not patented) and plants of the species *Peperomia graveolens*. 'Red Log' is distinguishable from 'Belly Button' by the following characteristics:

1. *Peperomia* 'Red Log' exhibits leaves that are dark green on the upper surface and red on the lower surface. In comparison, the leaves of 'Belly Button' are green on the upper surface and green on the lower surface.
2. *Peperomia* 'Red Log' exhibits smaller leaves than the leaves of 'Belly Button'.

'Red Log' is distinguishable from plants of the species *Peperomia graveolens* by the following characteristics:

1. *Peperomia* 'Red Log' exhibits leaves that are dark green on the upper surface and red on the lower surface. In comparison, plants of the species *Peperomia graveolens* have leaves that are green on the upper surface and red on the lower surface and are curved upwards.
2. *Peperomia* 'Red Log' exhibits leaves that are not smooth in texture. In comparison, plants of the species *Peperomia graveolens* have leaves that are succulent like and smooth in texture.
3. *Peperomia* 'Red Log' exhibits leaves that grow substantially perpendicular to the stem. In comparison, plants of the species *Peperomia graveolens* have leaves that are angled upward from the stem.

'Red Log' is distinguishable from the female parent plant, by the following characteristics:

1. *Peperomia* 'Red Log' exhibits leaves that are dark green on the upper surface and red on the lower surface. In comparison, the leaves of the female parent plant are green on the upper surface and green on the lower surface.
2. *Peperomia* 'Red Log' exhibits leaves that are more elongated that the leaves of the female parent plant. The leaves of the female parent plant are more round.

'Red Log' is distinguishable from the male parent plant by the following characteristics:

1. 'Red Log' exhibits dark green leaves on the upper surface and red on the lower surface. The leaves of the male parent plant are grey-green in color on both sides.
2. *Peperomia* 'Red Log' exhibits leaves that are not smooth in texture. In comparison, the leaves of the male parent plant are succulent like and smooth in texture.
3. *Peperomia* 'Red Log' exhibits an upright habit. In comparison, the habit of the male parent plant is more spreading.

BRIEF DESCRIPTION OF THE DRAWING

The accompanying photograph illustrates the distinguishing traits of *Peperomia* 'Red Log'. The photograph shows an overall view of a 30 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Peperomia* cultivar named 'Red Log'. Data was collected in Sappemeer, Netherlands from 30 week old plants grown in a glass greenhouse in 10.5 cm. diameter containers. The time of year was Summer and the temperature range was 18-25 degrees Centigrade during the day and 15-18 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'Red Log' has not been tested under all possible conditions and phenotypic differences may be observed with variations in environmental, climatic, and cultural conditions, however, without any variance in genotype.

Botanical classification: *Peperomia* hybrid 'Red Log'.
Annual or perennial: Perennial.
Parentage: 'Red Log' is a hybrid of the female parent, an unnamed *Peperomia verticillata* cultivar and the male parent an unnamed *Peperomia rubella* cultivar.
Plant type: Potted plant.
Growth habit: Broad spreading.
Plant shape: Flattened globe shaped.
Suitable container size: 7 cm. pots or larger.
Plant height: 8.2 cm.
Plant width: 15.7 cm.
Vigor: Low to moderate.
Low temperature tolerance: 10° Centigrade.
High temperature tolerance: 35° Centigrade.
Propagation: Leaf cuttings.
Time to initiate roots (summer): 10 days at 18 to 20° C.
Time to initiate roots (winter): 14 days at 18 to 20° C.
Time to produce a rooted cutting (summer): 80 days at 18 to 20° C.
Time to produce a rooted cutting (winter): 100 days at 18 to 20° C.
Growth rate: Low to moderate.
Crop time: Approximately 30 to 35 weeks in Sappemeer, Netherlands.
Root system: Fibrous.
Plant fragrance: None.
Stem:
- *Branching habit*.—Main branches only, no lateral braches.
- *Number of main branches per plant*.—Average 20.
- *Branch dimensions*.—6.8 cm. in length and 0.3 cm. in diameter.
- *Internode length*.—0.9 cm.
- *Stem shape*.—Rounded.
- *Stem luster*.—Slightly glossy.
- *Stem pubescence*.—Covered with very short hairs 0.1 mm. in length.
- *Stem angle*.—Average 30 degrees.
- *Stem strength*.—Strong.
- *Stem color* (*young*).—176C
- *Stem color* (*mature*).—178A.
- *Internode color*.—178A.

Foliage:
- *Leaf arrangement*.—Arranged in whorls of four.
- *Compound or single*.—Single.
- *Quantity of leaves per branch*.—Average 32.
- *Leaf shape*.—Broad obovate, succulent.
- *Leaf aspect*.—Moderately carinate.
- *Leaf apex*.—Broad acute.
- *Leaf base*.—Obtuse.
- *Leaf dimensions*.—2.0 cm. in length, 1.4 cm. in width and 0.2 cm. in thickness.
- *Texture*.—Velvety (both surfaces).
- *Leaf luster*.—Upper surface matte, lower surface slightly glossy.
- *Pubescence*.—Absent.
- *Leaf margin*.—Entire.
- *Venation pattern*.—Pinnate.
- *Young leaf color* (*upper surface*).—NN137C.
- *Young leaf color* (*lower surface*).—183C.
- *Mature leaf color* (*upper surface*).—Between 139A and N189A.
- *Mature leaf color* (*lower surface*).—183B.
- *Vein color* (*upper surface*).—144A.
- *Vein color* (*lower surface*).—N144A.

Petiole:
- *Petiole dimensions*.—0.3 cm. in length and 0.1 cm. in diameter.
- *Petiole texture*.—Glabrous.
- *Petiole luster*.—Matte.
- *Petiole pubescence*.—Absent.
- *Petiole strength*.—Low.
- *Petiole color*.—176B.

Flower: 'Red Log' has not produced flowers to date.
Fruit and seed: 'Red Log' has not produced fruit or seed to date.
Disease and pest resistance: Disease and pest resistance has not been observed.

The invention claimed is:

1. A new and distinct variety of *Peperomia* plant named 'Red Log' as described and illustrated.

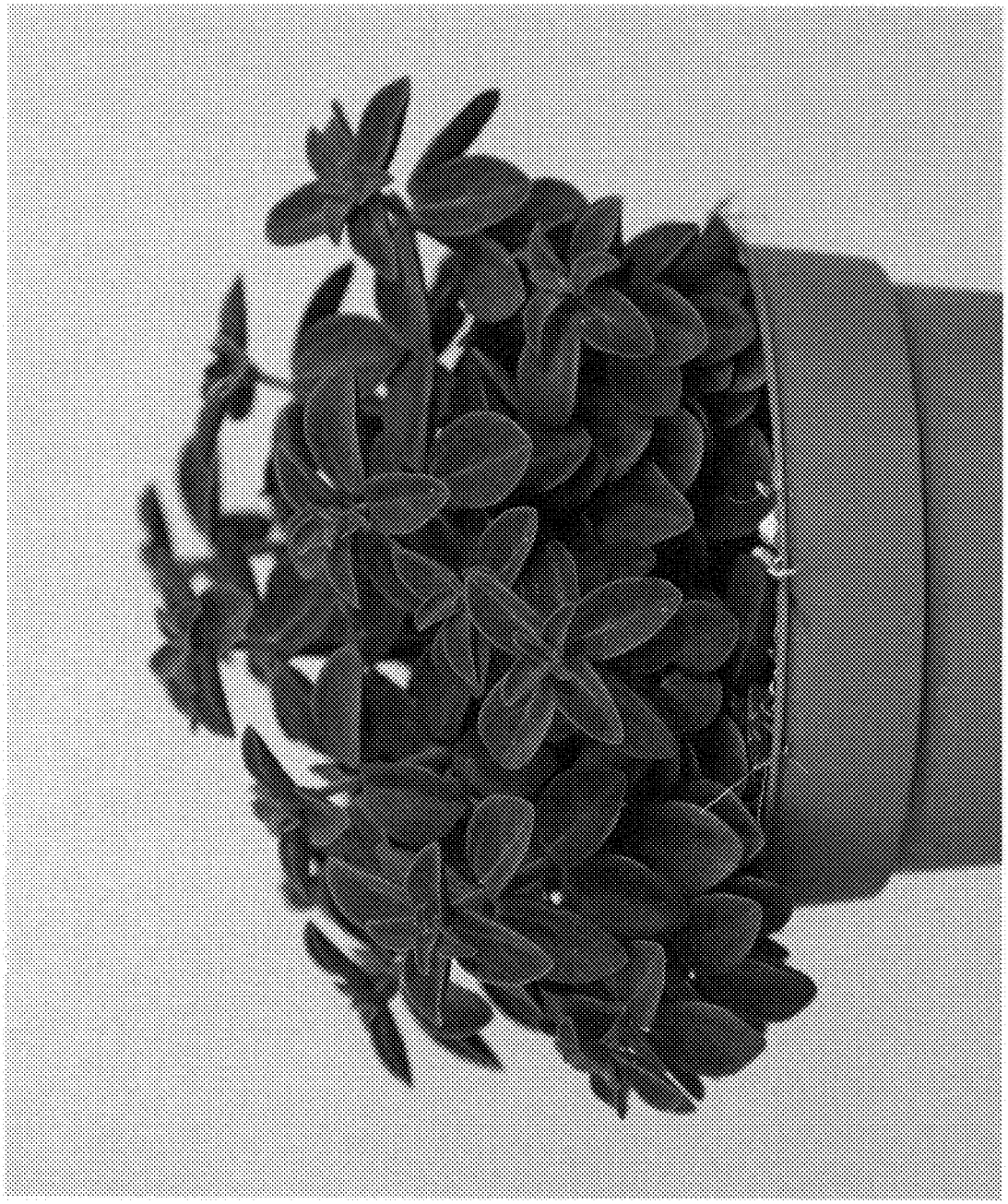

* * * * *